United States Patent
Rouland et al.

(10) Patent No.: US 11,110,116 B2
(45) Date of Patent: Sep. 7, 2021

(54) HYPEROSMOLAR COMPOSITION OF HYALURONIC ACID

(71) Applicant: Horus Pharma, Saint Laurent du Var (FR)

(72) Inventors: Jean-François Rouland, Lille (FR); Martine Claret, Saint Sulpice (CH); Claude Claret, Saint Sulpice (CH)

(73) Assignee: Horus Pharma, Saint Laurent du Var (FR)

( * ) Notice: Subject to any disclaimer, the term of this patent is extended or adjusted under 35 U.S.C. 154(b) by 0 days.

(21) Appl. No.: 16/439,804

(22) Filed: Jun. 13, 2019

(65) Prior Publication Data

US 2019/0307789 A1 Oct. 10, 2019

Related U.S. Application Data

(63) Continuation of application No. 15/301,045, filed as application No. PCT/EP2015/057186 on Apr. 1, 2015, now abandoned.

(30) Foreign Application Priority Data

Apr. 2, 2014 (FR) ..................................... 1452929

(51) Int. Cl.

| | | |
|---|---|---|
| *A61K 31/728* | (2006.01) | |
| *A61K 9/00* | (2006.01) | |
| *A61K 9/08* | (2006.01) | |
| *A61K 47/02* | (2006.01) | |
| *A61K 47/38* | (2006.01) | |

(52) U.S. Cl.
CPC .......... *A61K 31/728* (2013.01); *A61K 9/0048* (2013.01); *A61K 9/08* (2013.01); *A61K 47/02* (2013.01); *A61K 47/38* (2013.01)

(58) Field of Classification Search
None
See application file for complete search history.

(56) References Cited

U.S. PATENT DOCUMENTS

| | | |
|---|---|---|
| 2009/0111770 A1 | 4/2009 | Holzer et al. |
| 2010/0068300 A1 | 3/2010 | Koverech et al. |
| 2011/0105450 A1 | 5/2011 | Chapin et al. |
| 2011/0195925 A1 | 8/2011 | Liu et al. |
| 2016/0017254 A1 | 1/2016 | Cojocariu et al. |

FOREIGN PATENT DOCUMENTS

| | | | |
|---|---|---|---|
| EP | 0323522 A1 | 7/1989 | |
| EP | 2494954 B1 * | 4/2014 | .......... A61K 9/0048 |
| WO | 2008071524 A1 | 6/2008 | |
| WO | 2012/013736 A1 | 2/2012 | |
| WO | 2013/043832 A1 | 3/2013 | |

OTHER PUBLICATIONS

Pattini, DE 202011103553 U1, Nov. 10, 2011, machine translation. (Year: 2011).*
Knezovic, I. et al, Therapeutic Efficacy of 5% NaCl Hypertonic Solution in Patients with Bullous Keratopathy, Coll. Antropol., 2006, vol. 2, pp. 405-408.
Nagai et al. "An In Vitro Evaluation for Corneal Damages after Instillation of Eye Drops Using Rat Debrided Corneal Epithelium: Changes in Corneal Damage of Benzalkonium Chlloride by Addition of Thickening Agent". Yakugazu. Zasshi 132(7) 837-843 (2012) The Pharmaceutical Society of Japan.
Sill, Anne M. "Hyperosmotic agents for treatment of Fuchs' dystrophy" Resident's Corner. The AOA's CLCS Newsletter, Jan. 2013.
Yorek et al. "Corneal Sensivity to Hyperosmolar ye Drops: A Novel Behavioral Assay to Assess Diabetic Peripheral Neuropathy" IOVS, May 2016, vol. 57, No. 6, 2412-2419.
Bausch + Lomb, Muro 128 5% product page. Downloaded from the internet Jun. 2018.
Stanford Chemicals, Eye Drop Grade (Medical Grade) Hyaluronic Acid product page, published 2012.

* cited by examiner

*Primary Examiner* — Layla D Berry
(74) *Attorney, Agent, or Firm* — Banner & Witcoff, Ltd.

(57) ABSTRACT

The invention relates to a novel hyperosmolar composition of hyaluronic acid for the use thereof in the treatment of conical oedema.

15 Claims, No Drawings

HYPEROSMOLAR COMPOSITION OF HYALURONIC ACID

RELATED APPLICATIONS

This application is a Continuation Application of co-pending U.S. patent application Ser. No. 15/301,045, filed on Jan. 4, 2017, which is a National Stage Application under 35 U.S.C. 371 of co-pending PCT application PCT/EP2015/057186 designating the United States and filed Apr. 1, 2015; which claims the benefit of FR application number 1452929 and filed Apr. 2, 2014 each of which are hereby incorporated by reference in their entireties.

FIELD

The present invention concerns a novel hyperosmolar composition of hyaluronic acid for use in the treatment of corneal oedema.

BACKGROUND

Conical oedema results from an infiltration of liquid in the layers of the cornea. It appears as a thickening of the cornea with a loss of corneal transparency and a lowering of the visual acuity of the subject suffering from this affection. Common treatments of corneal oedema consist of the topical application of anti-inflammatory and anti-oedematous eye lotions, in particular hypertonic sodium chloride solutions. These treatments, however, which provide temporary relief for conical oedema subjects, prove to be not very effective for chronic oedemas since they do not prevent new infiltrations of liquid.

In the most serious cases, it is necessary to resort to surgical treatments, such as corneal transplantation, or laser treatments. It is thus important to be able to treat these oedemas effectively so as to avoid the recurrences and complications, which ultimately require recourse to these surgical treatments.

Saline compositions comprising hyaluronic acid are known in the state of the art. They are however "artificial tears", which are isotonic, or very slightly hypertonic, but very close to the osmolarity (isotonicity) of tears. For example, EP 323 522 describes several exemplary compositions identified as artificial tears comprising hyaluronic acid and sodium chloride, with an osmolarity ratio relative to isotonic saline solution of 1 to 1.1. These artificial tears are used to treat dry eye. WO 2013/043832 also describes an ophthalmic composition for treating recurrent corneal erosion (RCE) comprising, in particular, hyaluronic acid and sodium chloride. This composition is presented as hypertonic, but with an osmotic pressure between 320 to 350 mOsmol/kg, a pressure very close to an isotonic saline solution of the same order as that of the exemplary formulations of application EP 323 522. None of these saline solutions of hyaluronic acid has an osmolarity sufficient to treat corneal oedema, with no one even envisaging the use of hyaluronic acid in a hyperosmolar solution to treat corneal oedema.

BRIEF DESCRIPTION OF THE INVENTION

The present invention concerns a hyperosmolar ophthalmic composition comprising hyaluronic acid or an acceptable salt thereof and a hyperosmolarity agent, the composition having an osmolarity of 650 to 2000 mOsm/l.

The invention also concerns a hyperosmolar ophthalmic composition comprising hyaluronic acid or an acceptable salt thereof and a hyperosmolarity agent for use in the treatment of corneal oedema, and more particularly in the treatment of chronic corneal oedema (CCE).

DETAILED DESCRIPTION OF THE INVENTION

The object of the present invention is an ophthalmic composition, i.e. a composition intended to be applied to the eye of a human or animal subject, more particularly a human subject. Consequently, the ophthalmic composition must satisfy the specific technical characteristics of ophthalmic compositions, and more particularly those related to the selection of its components. These "ophthalmically acceptable" components must not, individually or combined in the composition, cause secondary reactions of the eye apart from the effect sought by the composition and the active agents thereof. The eye being an organ which is particularly sensitive to environmental stress, the composition must not cause parasitic irritations or allergic-type reactions to the detriment of the effect sought, more particularly in the case of ophthalmic compositions intended to treat an ophthalmic affection. The choice of the constituents of the composition is thus very important, which distinguishes the ophthalmic composition from a simple composition unsuited to ophthalmic use. The person skilled in the art is able to choose said components and to differentiate an ophthalmic composition from a simple composition intended for another use.

The ophthalmic composition preferably has a pH between 6 and 7. It thus usually comprises a buffer suitable for ophthalmic use, known to the person skilled in the art. Particular mention may be made of trisodium citrate dihydrate and citric acid monohydrate employed alone or in mixture.

The ophthalmic composition must also be sterile in order not to introduce pathogens likely to develop and to lead to ophthalmic complications. The term "sterile" is understood, within the meaning of the present invention, to mean the absence of germs within the meaning of the European Pharmacopoeia, 8th Edition (2014).

Many ophthalmic compositions comprise preservatives for preventing their contamination by germs, such as quaternary ammoniums, particularly benzalkonium chloride, alkyl-dimethyl-benzylammonium, cetrimide, cetylpyridinium chloride, benzododecinium bromide, benzethonium chloride, cetalkonium chloride, mercurial preservatives, such as phenylmercuric nitrate/acetate/borate, thiomersal, alcoholic preservatives, such as chlorobutanol, benzylic alcohol, phenylethanol, phenylethyl alcohol, carboxylic acids, such as sorbic acid, phenols, particularly methyl/propyl paraben, amidines, for example chlorhexidine digluconate and/or chelating agents such as EDTA alone or in combination with at least one other preservative.

The composition according to the invention is substantially free of such preservatives in order to satisfy a "preservative-free" indication. Its preservative content is 10 ppm or less, more particularly 1 ppm or less, preferentially equal to 0 ppm, with no preservative in its composition.

In the absence of preservatives, the ophthalmic composition must undergo a specific treatment during its preparation so as to avoid and prevent contamination by pathogens. In this sense, a preservative-free ophthalmic composition is distinguished from a simple composition comprising hyaluronic acid obtained without pointing out special precautions or describing the steps of the method making it possible to obtain this sterility characteristic of ophthalmic compositions.

Ophthalmic compositions are generally in the form of solutions, but also in the form of gels or ointments. The composition according to the invention is preferably a solution applied by placing one or more drops in the eye. The viscosity of the solution is nevertheless selected so as to allow it to remain on the eye, particularly on the cornea, for a period sufficient to allow it to act.

The ophthalmic composition according to the invention preferably has a viscosity of 15 to 100 centipoises. This viscosity is measured according to the recommendations of the European Pharmacopoeia 2.2.10, with a rotating viscometer, at 25° C., and 100 s$^{-1}$. Other measuring devices and methods suitable for measuring the viscosity of solutions are known to the person skilled in the art and provide similar results.

The viscosity of the ophthalmic composition according to the invention is due first to the amount of hyaluronic acid present. It is then adapted by adding "ophthalmic ally acceptable" viscosity agents. The person skilled in the art is well familiar with the viscosity agents able to be employed for the preparation of ophthalmic compositions and the amounts to be used to obtain the viscosity sought. Particular mention may be made of hydroxypropylmethylcellulose, hydroxyethylcellulose, carboxymethylcellulose, carbomers, agar gels, polyvinylpyrrolidone and polyvinyl alcohol.

Preferentially, the ophthalmic composition according to the invention comprises hydroxypropylmethylcellulose, preferentially in an amount of 0.05 to 0.5% by weight of hydroxypropylmethylcellulose, advantageously 0.1 to 0.4% by weight, more advantageously 0.2 to 0.3% by weight, particularly about 0.25% by weight.

Unless otherwise specified, the percentages are expressed by weight in relation to the total weight of the composition.

The composition according to the invention is a hyperosmolar composition. This hyperosmolarity is defined in relation to a standard value which is that of physiological saline representative of tear fluid. A "hyperosmolar" composition is also called "hypertonic". Physiological saline has an osmolarity value of 300 mOsm/l measured with an osmometer according to the method described in paragraph 2.2.35 of the European Pharmacopoeia. The ophthalmic composition according to the invention has an osmolarity of 650 to 2000 mOsm/l. Preferentially, the composition has an osmolarity greater than 1500 mOsm/l, more preferentially between 1600 and 1900 mOsm/l, advantageously about 1750 mOsm/l.

The person skilled in the art is well familiar with osmolarity agents for ophthalmic use. Particular mention may be made of sodium salts or potassium salts such as sodium chloride and potassium chloride and polyols such as glycerol. These osmolarity agents can be employed alone or in mixture, such as for example a mixture of potassium salts and sodium salts, for example NaCl+KCl, or a mixture of one or more salts and one or more polyols, such as the mixtures NaCl+glycerol, KCl+glycerol, or NaCl+KCl+glycerol. The person skilled in the art knows how to employ these osmolarity agents and the amounts to be employed in order to obtain the desired osmolarity ratio in the ophthalmic composition according to the invention, particularly also according to the viscosity sought.

According to a preferential embodiment of the invention, the osmolarity agent is sodium chloride. The ophthalmic composition advantageously comprises 2 to 10% by weight of sodium chloride, advantageously 4 to 6% by weight, more advantageously about 5% by weight.

The ophthalmic composition according to the invention comprises hyaluronic acid or a physiologically acceptable salt thereof. Advantageously, hyaluronic acid is present in the composition in the form of sodium hyaluronate.

The ophthalmic composition according to the invention being a preservative-free composition, it is necessary to treat it during its manufacture so as to avoid and prevent contamination by pathogens. These steps can have negative consequences on the composition, its turbidity or its stability over time. To meet the objective of the invention to prepare a hyperosmolar composition of hyaluronic acid, preferably preservative-free, it is advantageous to employ hyaluronic acid having an intrinsic viscosity of 1.4 to 1.9 m$^3$/kg.

The composition according to the invention preferentially comprises 0.01 to 0.025% by weight of hyaluronic acid, particularly in its sodium hyaluronate form, advantageously 0.1 to 0.2% by weight, particularly about 0.15% by weight.

According to a preferential embodiment of the invention, the composition comprises
  0.01 to 0.25% of sodium hyaluronate, particularly 0.1 to 0.2% by weight, more particularly about 0.15% by weight,
  2 to 10% of sodium chloride, particularly 4 to 6% by weight, more particularly about 5% by weight, and
  water.

According to a particular embodiment of the invention, the ophthalmic composition comprises
  hyaluronic acid or a physiologically acceptable salt thereof
  one or more osmolarity agents
  a buffer to maintain a pH between 6 and 7, and
  water,
the constituents and the amounts thereof being advantageously selected by the person skilled in the art in order to obtain an osmolarity of 650 to 2000 mOsm/kg, advantageously greater than 1500 mOsm/l, preferentially between 1600 and 1900 mOsm/l, more preferentially about 1750 mOsm/l, and a viscosity of 15 to 100 centipoises.

According to a more preferential embodiment of the invention, the ophthalmic composition consists of
  0.01 to 0.25% of sodium hyaluronate, particularly 0.1 to 0.2% by weight, more particularly about 0.15% by weight,
  2 to 10% of sodium chloride, particularly 4 to 6% by weight, more particularly about 5% by weight,
  0.05 to 0.5% of HPMC, particularly 0.1 to 0.4% by weight, more particularly 0.2 to 0.3% by weight, even more particularly about 0.25% by weight,
  a buffer for a pH between 6 and 7, and
  water.

The invention also concerns a method for manufacturing an ophthalmic composition as defined above and in the examples. The ophthalmic composition according to the invention combines several difficulties with regard to its preparation since it is a solution which:
  contains hyaluronic acid,
  with a high concentration of osmolarity agent, and
  does not contain preservatives.

The method according to the invention advantageously comprises the following steps:
  Preparation of a first aqueous solution comprising the hyperosmolarity agent and if need be one or more viscosity agents and/or one or more buffers (solution B), Preparation of a second aqueous solution comprising hyaluronic acid or an acceptable salt thereof (solution A), Transfer of solution A into solution B, If need be adjustment of the pH, Homogenization of the solution and if need be final adjustment of the pH, and Sterilizing filtration.

The various steps for preparing solutions, homogenization and sterilizing filtration are well-known to the person skilled in the art. The composition obtained is preferably packaged in sterile packaging, advantageously in devices suited to its preservation and use.

The composition according to the invention is packaged in a suitable device allowing both its preservation protected from contamination by pathogens and the release of a suitable amount of the composition when applied on the eye, preferably in the lower conjunctival sac.

The release is achieved in the form of drops. Preferably, the device for packaging and dispensing the composition according to the invention make it possible to release drops weighing between 0.03 and 0.15 g.

The invention also concerns the ophthalmic composition as defined above and in the examples, for use in the treatment of conical oedema, more particularly for the treatment of chronic corneal oedema (CCE).

The treatment usually consists in instilling 1 to 2 drops of the composition according to the invention up to 4 times per day, preferably beginning in the morning upon the waking of the subject with corneal oedema, particularly with CCE.

The interval between the applications is between 15 minutes and 3 hours, preferably about 30 minutes, ranging between 1 to 2 hours, on average 90 minutes between each application, more preferentially about 30 minutes.

Advantageously, the treatment comprises a first application in the eye of the subject with corneal oedema, more particularly with CCE, of a suitable dose of the composition followed by a second application of a suitable dose.

The second application can take place 1 with 2 hours after the first application. It can also take place preferably 30 minutes after the first application.

The suitable dose corresponds to 1 or 2 drops of the composition.

The treatment advantageously comprises a third application of a suitable dose, preferably 30 minutes after the second application, ranging up to 1 to 2 hours after the second application, optionally followed by a fourth application of a suitable dose, preferably 30 minutes after the third application, ranging up to 1 to 3 hours after the third application.

According to a particular embodiment of the invention, the treatment comprises the application in the eye of the subject with conical oedema, more particularly with CCE, of a suitable dose of the composition repeated at least 3 times per day, preferably 4 times per day, with an interval between the applications between 15 minutes and 3 hours, preferably about 30 minutes, ranging from 1 to 2 hours, on average 90 minutes between each application, more preferentially about 30 minutes.

Preferentially, the first application takes place in the morning when the patient awakens or shortly thereafter.

The invention also concerns a method for treating corneal oedema, particularly chronic corneal oedema, in a subject having corneal oedema, said method consisting in applying in the eye of said subject one or more drops of the composition according to the invention, according to the therapeutic regimens described above.

In particular, the present invention concerns a method for treating conical oedema in a corneal oedema patient, the method comprising the application in the eye of the subject with conical oedema, more particularly with CCE, of a suitable dose of the composition according to the invention repeated at least 3 times per day, preferably 4 times per day.

The interval between the applications is preferably about 30 minutes, ranging from 1 to 2 hours, on average 90 minutes between each application.

Advantageously, the first application takes place in the morning when the patient awakens or shortly thereafter.

The application of the composition is achieved by the instillation of drops, preferably in the lower conjunctival sac of the eye, with the subject looking upward and while pulling the lower lid slightly downward. After the instillation, it is recommended to keep the eye closed for 1 to 2 minutes.

For a CCE subject, the treatment is advantageously given for a period of at least 2 weeks, ranging up to 4 weeks or more. The composition according to the invention is particularly suited to a long-term treatment, i.e. ranging up to several months.

EXAMPLES

Example 1—Composition

An ophthalmic composition comprising the following components is prepared:

| Ingredients | % | Role |
| --- | --- | --- |
| Water for injection | 92.14 | Excipient |
| Sodium chloride | 5.00 | Hyperosmolarity agent |
| Trisodium citrate dihydrate | 1.45 | Buffer |
| Citric acid monohydrate (1% solution) | 1.01 | Buffer |
| HPMC | 0.25 | Thickening agent |
| Sodium hyaluronate | 0.15 | Lubricating agent |

The pH is buffered between 6.2 and 6.8.

The composition is prepared according to the following procedure.

Dissolution of Raw Materials:

Preparation of solution B

HPMC is added with stirring to heated purified water. The solution is then cooled to room temperature. Trisodium citrate dihydrate is then added with stirring until complete dissolution, then sodium chloride until complete dissolution, then citric acid until complete dissolution.

Preparation of solution A

Sodium hyaluronate is added slowly and with stirring to purified water. Stirring is maintained for several hours until complete dissolution of the sodium hyaluronate.

Transfer of solution A into solution B

Adjustment of the pH between 6.2 and 6.8

Final homogenization and final adjustment of the pH

Sterilizing filtration with a sterilizing filter provided with a 0.22 µm hydrophilic cartridge Filling of sterile containers.

The solution obtained has an osmolarity of 1750 mOsm/kg (±150). It is stored in sterile containers. It remains stable at room temperature up to at least 24 months, and 1 month after opening.

Example 2—Treatment of CCE

A clinical trial involving 20 patients with diagnosed corneal oedema, linked to endothelial insufficiency, was carried out over a period of 28 days. One to two drops were instilled 4 times per day in the affected eye, at 90-minute intervals, beginning with the first instillation at 8:15 in the morning. The average age of the patients was 72.2 years.

The evolution of visual acuity (measured with the ETDRS scale) and conical thickness (measured by ultrasonic pachymetry) was evaluated by comparing the values between the inclusion visit (7 days before the beginning of the treatment) and the follow-up visits (7 and 28 days after the first day of treatment).

As of the seventh day of treatment, visual acuity improves significantly by 5 letters on average (p<0.001, paired Wilcoxon test). Conical thickness also decreased significantly (p=0.033, paired Wilcoxon test). The functional improvement is found at 28 days of instillation. No undesirable effect was observed during the study. After 28 days of treatment, the hyperosmolar solution without preservative and containing sodium hyaluronate significantly improved visual acuity of the patients and was very well tolerated.

The invention claimed is:

1. A hyperosmolar ophthalmic composition comprising 0.01 to 0.2% by weight of sodium hyaluronate, 0.05 to 0.5% by weight of hydroxypropylmethyl cellulose and sodium chloride as a hyperosmolarity agent, wherein the hyperosmolar ophthalmic composition has an osmolarity of 1500 to 2000 mOsm/l and a viscosity of 15 to 100 centipoises.

2. The composition according to claim 1, further comprising a hyperosmolarity agent selected from the group consisting of potassium chloride and glycerol and mixtures thereof.

3. The composition according to claim 2 wherein said sodium chloride is present in an amount of 4 to 6% by weight of the composition.

4. The composition according to claim 1 wherein the sodium hyaluronate has an intrinsic viscosity of 1.4 to 1.9 m³/kg.

5. The composition according to claim 1 further comprising a viscosity agent selected from the group consisting of hydroxyethylcellulose, carboxymethylcellulose, carbomers, agar gels, polyvinylpyrrolidone and polyvinyl alcohol.

6. A method for treating corneal oedema in a subject in need thereof, said method comprising applying in the eye of said subject one or more drops of the hyperosmolar ophthalmic composition of claim 1.

7. The method according to claim 6, wherein the corneal oedema is a chronic corneal oedema (CCE).

8. The method according to claim 6, wherein the treatment comprises a first application in the eye of the subject of a suitable dose of the composition followed by a second application of a suitable dose 30 minutes to 90 minutes after the first application.

9. The method according to claim 8, wherein it comprises a third application of a suitable dose 30 minutes to 90 minutes after the second application.

10. The method according to claim 6, wherein the treatment comprises the application in the eye of the subject of a suitable dose of the composition repeated at least 3 times per day, with an interval between the applications of 30 minutes to 90 minutes.

11. The method according to claim 10, wherein the first application is given when the patient awakens in the morning or shortly thereafter.

12. The method according to claim 6, wherein the treatment is given for a period of at least 2 weeks, ranging up to at least 4 weeks.

13. The method according to claim 1, wherein said composition further includes an osmolarity agent selected from the group consisting of potassium chloride, glycerol and mixtures thereof.

14. The method according to claim 1 wherein said composition further comprises a viscosity agent selected from the group consisting of hydroxyethylcellulose, carboxymethylcellulose, carbomers, agar gels, polyvinylpyrrolidone and polyvinyl alcohol.

15. A hyperosmolar ophthalmic composition having an osmolarity of 1500 to 2000 mOsm/l, and comprising 4 to 6% by weight of the composition of sodium chloride as hyperosmolarity agent, 0.01 to 0.25% by weight of sodium hyaluronate and 0.05 to 0.5% by weight of hydroxypropylmethyl cellulose.

* * * * *